United States Patent [19]

Hogin

[11] 4,354,494
[45] Oct. 19, 1982

[54] CONDOM HAVING A RETENTION STRAP

[76] Inventor: Philip E. Hogin, Mooreland Rd., Greenwich, Conn. 06830

[21] Appl. No.: 242,036

[22] Filed: Mar. 9, 1981

[51] Int. Cl.³ .............................................. A61F 5/42
[52] U.S. Cl. .................................... 128/294; 128/79; 128/132 R
[58] Field of Search ..................... 128/79, 132 R, 294, 128/295; 206/438, 303, 494, 69; 116/200, 327

[56] References Cited

U.S. PATENT DOCUMENTS

| | | | |
|---|---|---|---|
| 1,935,970 | 11/1933 | Wooster et al. | 116/200 |
| 2,332,857 | 10/1943 | Karg | 206/69 |
| 3,136,417 | 6/1964 | Clinch | 206/69 |

FOREIGN PATENT DOCUMENTS

| | | | |
|---|---|---|---|
| 120453 | 5/1901 | Fed. Rep. of Germany | 128/294 |
| 445166 | 5/1927 | Fed. Rep. of Germany | 128/79 |
| 867582 | 1/1953 | Fed. Rep. of Germany | 128/294 |

*Primary Examiner*—Richard J. Apley
*Assistant Examiner*—J. L. Kruter
*Attorney, Agent, or Firm*—St. Onge, Steward, Johnston & Reens

[57] ABSTRACT

A condom for preventing conception or venereal infection during coitus comprising an elongate and tubular sheath being closed at one end and having an opening at the other end thereof, said opening including a periphery, and an elongate resilient retention strap for retaining said tubular sheath on a penis inserted therein, said strap having one end portion attached to said periphery at one point and having another end portion attached to said periphery at another point spaced from said one point, said retention strap being adapted to be stretched to fit behind the scrotum. The tubular sheath together with said retention strap is capable of being rolled into a generally circular flat disc to provide ease of packaging and for ease of application.

6 Claims, 4 Drawing Figures

CONDOM HAVING A RETENTION STRAP

BACKGROUND OF THE INVENTION

1. Field of the Invention

The present invention relates generally to the field of contraceptive and prophylactic devices and, more particularly, to condoms for preventing conception and venereal infection during coitus.

2. Description of the Prior Art

A conventional condom comprises an elongate thin tubular sheath made of resilient material. The sheath is closed at one end and open at the other to provide for insertion of a penis. The condom is typically rolled into a relatively thin disc during manufacture thereof to provide for compact storage of the condom and to provide for ease of application of the condom. Conventional condoms are considered to be very effective in preventing unwanted conception and transmission of venereal diseases. However, during coitus, a conventional condom tends to slip with respect to the penis therein, particularly in the case where the condom is internally lubricated. This slippage has the obvious disadvantages of discomfort to the male and the female and the risk that the condom may slip sufficiently to allow leakage of semen. Further, a conventional condom, which tends to function best with a fully erect penis, may slip with respect to a partially erect penis. It should be understood that after ejaculation during coitus and while the penis is left in the vagina, the penis may tend to soften and thus the condom may slip with respect to the penis thereby causing unwanted leakage of semen or incursion of infectious matter.

U.S. Pat. No. 3,759,254 discloses a contraceptive device having a sack at the open end thereof which acts to maintain the tubular member in place during copulation so that a tight-fitting conventional condom is not required. The device disclosed in this patent has several drawbacks including that the sack portion is not adapted to be rolled or convoluted, and that the thickness of the wall is preferably greater than a conventional condom to allow the appliance to function as a prosthetic. It should be understood that the inability to be rolled is a significant drawback in that condoms are typically mass produced and are rolled into disc-shaped forms that fit within compact packaging. Furthermore, a rolled condom is relatively simple to apply.

Additional types of devices applied to a penis are disclosed in U.S. Pat. No. 3,633,572; U.S. Pat. No. 713,900; U.S. Pat. No. 2,123,109; U.S. Pat. No. 87,932; and German Patentschrift No. 120.453.

SUMMARY OF THE INVENTION

A condom in accordance with the present invention comprises an elongate thin tubular sheath made of resilient material, such as, for example, rubber. The sheath is closed at one end and has an opening at the other end for receiving a penis. The opening includes a periphery preferably having a peripheral bead. An elongate resilient retention strap is provided to secure the sheath during coitus. One end portion of the retention strap is attached to the periphery at one point and another end portion of the strap is attached to said periphery on another point spaced from the one point. The retention strap, once the sheath portion of the condom is in place, is stretched and placed behind the scrotum so that during coitus the sheath is retained on the penis.

A condom is accordance with the present invention may be rolled into a flat disc shape to provide for compact packaging and application of the condom. The structure and advantage of a condom in accordance with the present invention will be apparent from the following detailed description of the preferred embodiment with reference to the drawings.

DETAILED DESCRIPTION OF THE INVENTION

Figure 1:
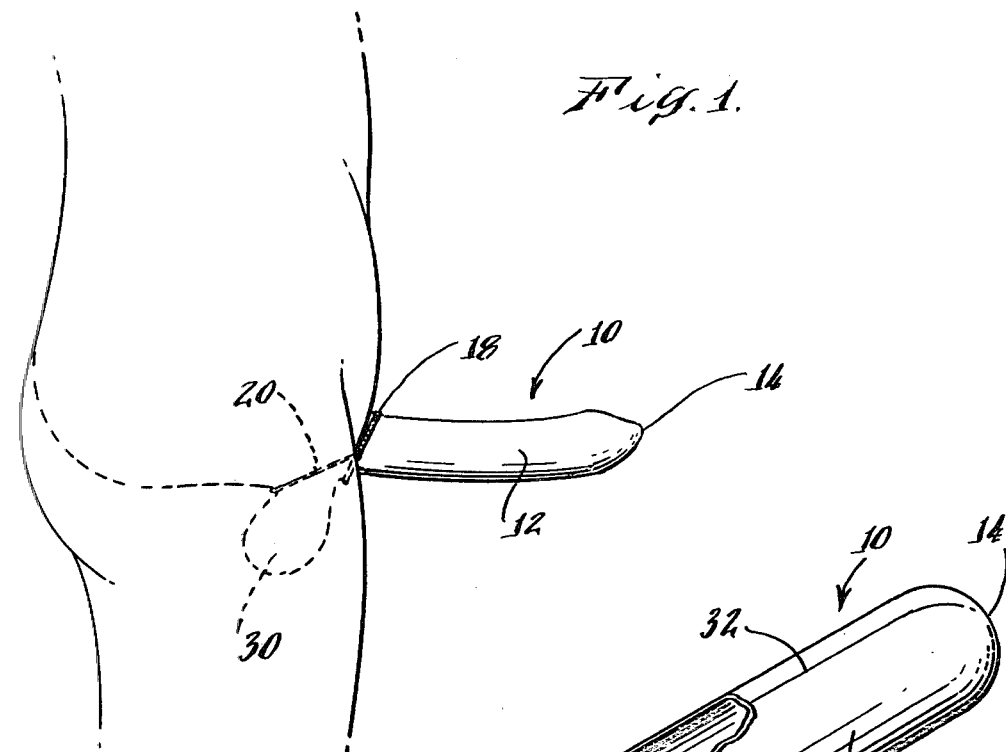
FIG. 1 is a side plan view of a condom in accordance with the present invention placed on a male.
Figure 2:
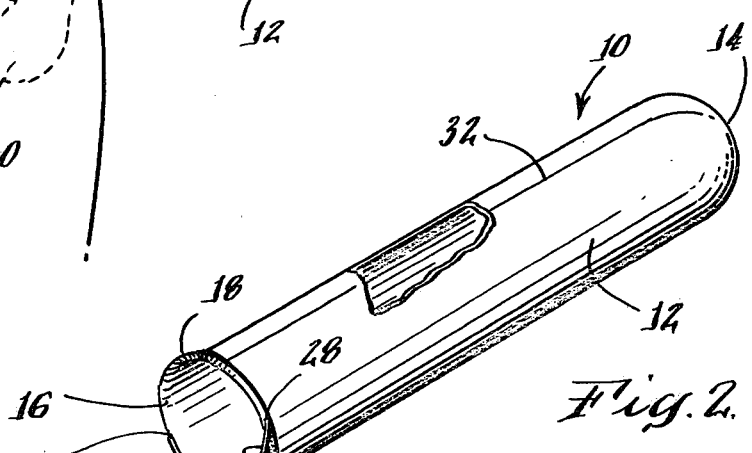
FIG. 2 is a perspective view of the condom shown in FIG. 1.
Figure 3:
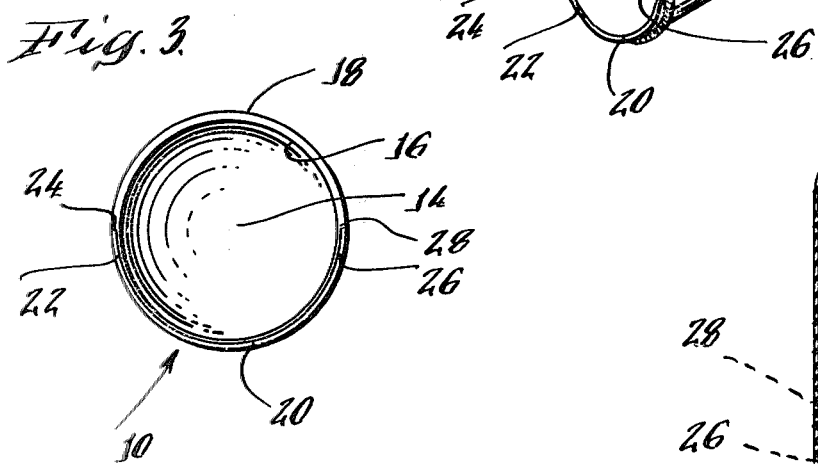
FIG. 3 is a rear plan view looking into the open end of the condom shown in FIG. 2.

Referring to FIGS. 1-3, a condom 10 in accordance with the present invention comprises an elongate thin tubular sheath 12 made of resilient material such as, for example, rubber. Sheath 12 is closed at one end 14 and has an opening 16 having a periphery 18, preferably in the form of a beaded edge, at the other end thereof.

A retention strap 20 made of a resilient material includes one end portion 22 attached to the periphery 18 at one point 24 and has another end portion 26 attached to the periphery 18 at another point 28 spaced from point 24. Preferably, the points 24 and 28 are diametrically opposed. In one embodiment of the invention the end portions 22 and 26 of strap 20 are integral with the periphery 18 of the sheath 12.

In accordance with one aspect of the invention, the cross-sectional area of the upper part of bead 18 is approximately equal to the combined cross-sectional areas of lower part of the bead and the retention strap. It is preferred that the retention strap when in a relaxed condition lie adjacent the lower part of the bead (FIG. 2 shows the strap 20 pulled slightly away from the lower part of the bead to enable the strap to be seen as being distinct from the lower part of the bead). Further, it is also preferred that the diameter of the lower part of the bead be approximately equal to the diameter of the strap.

Figure 4:
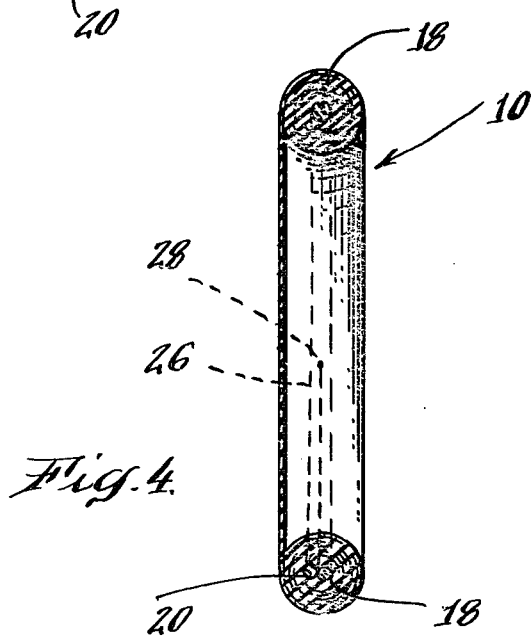
FIG. 4 is a sectional view of the condom shown in FIGS. 2 and 3 after it has been rolled.

Referring in particular to FIG. 4, the condom shown in FIGS. 2 and 3 is rolled in a disc shaped configuration to enable ease of packaging and distribution. As shown in the bottom portion of FIG. 4, the strap 20 may be rolled jointly with bead 18 to form a compact disc-shaped condom. Referring to FIGS. 1 and 4, the manner by which the condom 10 is applied to the penis will now be described. The head of the penis is pressed against end 14 of condom and the condom is unrolled along the shaft of the penis until strap 20 is free. To enable the man applying the rolled condom to distinguish the upper part of the condom from the lower part so that when the condom is unrolled the strap is in the correct position, a means for visually indicating the upper part of the condom is provided. Referring to FIG. 2, a line 32 is printed from the tip of the condom on condom end 14 along the uppermost length of sheath 12. The condom is unrolled so that the line 32 is disposed along the top length of the penis. Strap 20 is then pulled downwardly and stretched to enable the strap to be fit over scrotum 30. When strap 20 is released, it snuggly wraps around the scrotum 30 and holds the sheath 12 of the condom in position with respect to the penis.

A condom in accordance with the present invention has the advantage that it is retained on the penis during and after coitus and can be packaged in a rolled disc form. It is also retained during temporary relaxation and subsequent repeated erection of a penis. The sheath 12 has been shown in the drawings as a smooth sheath simply because this is the most common form. It should be understood, however, that the sheath may have mechanical formations to provide stimulation during coitus. The condom in accordance with the present invention is adaptable to various sized penises since the sheath will be retained by strap 20. Further, a condom in accordance with the present invention may be applied prior to erection so that interruption of foreplay to apply the condom may be avoided.

It should be understood that a condom in accordance with the present invention is particularly suitable for use with lubricants because the strap 20 retains condom when a conventional lubricated condom would have a tendency to slip. When a conventional lubricated condom is rolled for packaging, the lubricant, which is desirable on the outside to assist in penetration, is unavoidably applied to the inside of the condom, thus encouraging slippage that is prevented by the retention strap of a condom in accordance with the present invention.

The resilient material specified, that is rubber, is not a critical material and any material having similar characteristics may be substituted therefore. Although one embodiment of the invention has been described in detail, it should be understood that modifications and other embodiments incorporating the inventive features may be constructed. It is intended that the foregoing disclosure be considered as illustrating the principles of the present invention.

What is claimed is:

1. A condom comprising:
    an elongate thin tubular sheath of resilient material being closed at one end and having an opening at the other end, said opening including a periphery; and
    a resilient retention strap having one end portion attached to said periphery at one point and having another end portion attached to said periphery at another point spaced from said one point, said periphery including a beaded edge, said end portions being formed integrally with said edge, said beaded edge comprising an upper part and a lower part each having a cross-sectional area and wherein said resilient strap has a cross-sectional area, said cross-sectional area of said upper part being approximately equal to the combined cross-section areas of said lower part and said strap.

2. A condom according to claim 1 wherein said points of attachment are located diametrically opposed to one another.

3. A condom according to claim 1 wherein said resilient retention strap when in a relaxed position lies adjacent said lower part of the bead.

4. A condom according to claim 1 wherein said cross-sectional areas of said lower part and said strap are approximately equal.

5. A condom according to claim 1 and further including means for visually indicating the upper part of said condom.

6. A condom according to claim 5 wherein means for visually indicating comprises line extending from said closed end along the uppermost length of said sheath.

* * * * *